(12) United States Patent
Sarshogh et al.

(10) Patent No.: US 12,327,616 B2
(45) Date of Patent: Jun. 10, 2025

(54) PRE-TRAINING MOLECULE EMBEDDING GNNS USING CONTRASTIVE LEARNING BASED ON SCAFFOLDING

(71) Applicant: MICROSOFT TECHNOLOGY LICENSING, LLC, Redmond, WA (US)

(72) Inventors: Mohammad Reza Sarshogh, Seattle, WA (US); Robin Abraham, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 696 days.

(21) Appl. No.: 17/708,384

(22) Filed: Mar. 30, 2022

(65) Prior Publication Data

US 2023/0230662 A1 Jul. 20, 2023

Related U.S. Application Data

(60) Provisional application No. 63/301,177, filed on Jan. 20, 2022.

(51) Int. Cl.
*G16C 20/30* (2019.01)
*G06N 3/08* (2023.01)
*G16C 20/40* (2019.01)
*G16C 20/70* (2019.01)

(52) U.S. Cl.
CPC ............ *G16C 20/30* (2019.02); *G06N 3/08* (2013.01); *G16C 20/40* (2019.02); *G16C 20/70* (2019.02)

(58) Field of Classification Search
None
See application file for complete search history.

(56) References Cited

U.S. PATENT DOCUMENTS

| | | | | |
|---|---|---|---|---|
| 8,595,154 | B2* | 11/2013 | Breckenridge | G06N 20/00 706/12 |
| 11,127,488 | B1* | 9/2021 | Bajpai | G16C 20/50 |
| 11,144,790 | B2* | 10/2021 | Li | G06N 3/084 |
| 11,288,575 | B2* | 3/2022 | Tomioka | G06N 3/063 |
| 11,500,905 | B2* | 11/2022 | Baughman | G06F 16/285 |

(Continued)

OTHER PUBLICATIONS

"Losses-PyTorch Metric Learning", Retrieved from: https://web.archive.org/web/20210330140241/https://kevinmusgrave.github.io/pytorch-metric-learning/losses/, Mar. 30, 2021, 30 Pages.

(Continued)

*Primary Examiner* — Maikhanh Nguyen
(74) *Attorney, Agent, or Firm* — Workman Nydegger (57) ABSTRACT

Systems and methods are provided for generating a training dataset for training a molecule embedding module using contrastive learning, wherein the definition of similarity is based on molecular scaffold similarity. For example, systems access a molecular dataset and separate the molecular dataset into positive samples and negative samples. Systems then generate a training dataset comprising the positive samples and negative samples. Systems and methods are also provided for using the trained molecule embedding module to generate molecule embeddings and for building an end-to-end machine learning model configured to perform molecular embedding analysis and molecular property prediction, the model comprising the trained molecule embedding module and a property prediction module.

8 Claims, 9 Drawing Sheets

(56) References Cited

U.S. PATENT DOCUMENTS

| | | | | |
|---|---|---|---|---|
| 11,720,813 B2* | 8/2023 | Babu | ................... | G06N 20/20 |
| | | | | 706/12 |
| 11,762,635 B2* | 9/2023 | Brown | ................... | G06N 5/04 |
| | | | | 706/12 |
| 11,763,599 B2* | 9/2023 | Wang | ................... | G06F 18/217 |
| | | | | 382/118 |
| 2020/0105375 A1* | 4/2020 | Pan | ................... | G16B 40/20 |
| 2020/0388401 A1* | 12/2020 | Spiro | ................... | G16H 20/10 |
| 2021/0004670 A1* | 1/2021 | Tripathi | ................... | G06N 3/084 |
| 2021/0081804 A1* | 3/2021 | Stojevic | ................... | G06N 3/088 |
| 2022/0198286 A1* | 6/2022 | Prat | ................... | G06V 10/82 |

OTHER PUBLICATIONS

"RDKit: Open-Source Cheminformatics Software", Retrieved from: https://web.archive.org/web/20220316172251/https://www.rdkit.org/, Mar. 16, 2022, 2 Pages.

"SMILES Tutorial", Retrieved from: https://web.archive.org/web/20170127075822/https://archive.epa.gov/med/med_archive_03/web/html/smiles.html, Jan. 27, 2017, 3 Pages.

Brody, et al., "How Attentive are Graph Attention Networks?", In repository of arXiv:2105.14491v3, Jan. 31, 2022, 26 Pages.

Chen, et al., "A Simple Framework for Contrastive Learning of Visual Representations", In Proceedings of the International Conference on Machine Learning, Nov. 21, 2020, 11 Pages.

Cho, et al., "Learning Phrase Representations using RNN Encoder-Decoder for Statistical Machine Translation", In Repository of arXiv:1406.1078v3, Sep. 3, 2014, 15 Pages.

Corso, et al., "Principal Neighbourhood Aggregation for Graph Nets", In Journal of Advances in Neural Information Processing Systems, 2020, 12 Pages.

Gilmer, et al., "Neural Message Passing for Quantum Chemistry", In Proceedings of the 34th International Conference on Machine Learning, Jul. 17, 2017, 10 Pages.

He, et al., "Momentum Contrast for Unsupervised Visual Representation Learning", In Proceedings of IEEE/CVF Conference on Computer Vision and Pattern Recognition, Jun. 13, 2020, pp. 9726-9735.

Hu, et al., "Strategies for Pre-Training Graph Neural Networks", In repository of arXiv:1905.12265v3, Feb. 18, 2020, 22 Pages.

Jiménez-Luna, et al., "Artificial intelligence in drug discovery: recent advances and future perspectives", In journal of Expert opinion on drug discovery, vol. 16, Issue 9, Sep. 2, 2021, pp. 949-959.

Kipf, et al., "Semi-Supervised Classification with Graph Convolutional Networks", In Repository of arXiv:1609.02907, Feb. 22, 2017, 14 Pages.

Li, et al., "Gated Graph Sequence Neural Networks", In repository of arXiv:1511.05493v4, Sep. 22, 2017, 20 Pages.

Li, et al., "Learn molecular representations from large-scale unlabeled molecules for drug discovery", In repository of arXiv:2012.11175v1, Dec. 21, 2020, 20 Pages.

Liu, et al., "N-Gram Graph: Simple Unsupervised Representation for Graphs, with Applications to Molecules", In Journal of Advances in Neural Information Processing Systems, 2019, 13 Pages.

Oord, et al., "Representation Learning with Contrastive Predictive Coding", In Repository of arXiv:1807.03748v1, Jul. 10, 2018, 13 Pages.

Rong, et al., "Self-supervised Graph Transformer on Large-scale Molecular Data", In Proceedings of the 34th International Conference on Neural Information Processing Systems, Dec. 2020, 13 Pages.

Sutskever, et al., "Sequence to Sequence Learning with Neural Networks", In Proceedings of Advances in neural information processing systems, Sep. 10, 2014, 9 Pages.

Wang, et al., "Molecular Contrastive Learning of Representations via Graph Neural Networks", In repository of arXiv:2102.10056v2, Jan. 17, 2022, 19 Pages.

Zhu, "Dual-view Molecule Pre-training", In repository of arXiv:2106.10234v2, Oct. 13, 2021, 15 Pages.

"ImageNet", Retrieved from: https://web.archive.org/web/20211021000659/https://www.image-net.org/, Oct. 21, 2021, 1 Page.

Gawehn, et al., "Deep Learning in Drug Discovery", In Journal of Molecular Informatics, vol. 35, Issue 1, Jan. 2016, pp. 3-14.

U.S. Appl. No. 63/301,177, filed Jan. 20, 2022.

"International Search Report and Written Opinion Issued in PCT Application No. PCT/US22/052916", Mailed Date: Apr. 19, 2023, 11 Pages.

* cited by examiner

PRE-TRAINING MOLECULE EMBEDDING GNNS USING CONTRASTIVE LEARNING BASED ON SCAFFOLDING

CROSS-REFERENCE TO RELATED APPLICATIONS

This application claims the benefit of and priority to U.S. Provisional Patent Application Ser. No. 63/301,177 filed on Jan. 20, 2022, and entitled "PRE-TRAINING MOLECULE EMBEDDING GNNS USING CONTRASTIVE LEARNING BASED ON SCAFFOLDING," which application is expressly incorporated herein by reference in its entirety.

BACKGROUND

Quantitative representation of molecules is very useful for computer-aided chemical discoveries, particularly where molecules are embedded as numerical vectors in an N-dimensional Euclidean space in support of molecular grouping, differentiating, and property prediction. However, learning how to map molecule space to an N-dimensional Euclidean space is a difficult task and there are several limitations to existing approaches.

Some conventional methods for training a machine learning model to generate molecular embeddings include unsupervised training techniques. In one approach, called context prediction, is a contrastive learning method. The pre-training of the molecule embedding module is based on mapping a node embedding (i.e., atom embedding) and its aggregated K-hope neighborhood embedding (e.g., context embedding, connected atoms) close to each other. Another approach, called attribute masking, is based on node (i.e., atom) and edge attribute (i.e., bond properties) masking during training. Both of these approaches require pre-processing of the data and assumes that for the negative sample selection process different nodes with have different contexts. However, having to pre-process the data is both time and computational expensive, and there are circumstances in which different nodes may have similar contexts. Another contrastive approach is achieved by generating positive example using atom masking, bond deletion, and sub-graph removal.

These approaches can degrade the overall quality and accuracy of the results returned when the systems receive queries against the molecular data. Additionally, these conventional techniques can limit and degrade the quality of downstream tasks and applications, such as searching for drugs similar to a target drug and predicting drug-to-drug interactions when systems are using only the fragmented molecular embedding data.

Accordingly, there is an on-going need and desire for improved systems, methods, and devices for molecular embedding generation, and particularly, for improved systems, methods, and devices that can be utilized to improve training for molecular similarity analysis, so as to more efficiently and effectively perform molecular similarity, drug similarity and drug interaction prediction.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Embodiments disclosed herein relate to systems, methods, and devices that are configured for generating a training dataset for training a molecule embedding module using contrastive learning, wherein the definition of similarity is based on molecular scaffold similarity.

Disclosed systems are configured to access a molecular dataset comprising a plurality of molecules and separate the molecular dataset into a plurality of positive samples and a plurality of negative samples. This is achieved by accessing a molecular scaffold dataset comprising a plurality of molecular scaffolds. Each molecular scaffold defines a core structure of a particular molecule and one or more underlying characteristics of the particular molecule. The systems are also configured to determine that at least two molecules are similar based on the at least two molecules corresponding to a same molecular scaffold and label the at least two molecules that are determined to be similar as a positive sample, as well as to determine that at least two other molecules are dissimilar based on the at least two other molecules each corresponding to different molecular scaffolds and label those molecules that are determined to be dissimilar as a negative sample.

Subsequent to separating the molecular dataset into positive and negative samples, disclosed systems are configured to generate a training dataset comprising the plurality of positive samples corresponding to pairs of similar molecules and the plurality of negative samples corresponding to pairs of dissimilar molecules.

Once the training dataset is generated, it can be selectively used to train a molecule embedding module.

Disclosed systems are also directed to systems and methods for identifying positive samples from a set of molecule samples in order to map similar molecules to each other in a molecular embedding space. In such embodiments, for example, systems are configured to access a molecule embedding module that has been previously trained to map similar molecules close together in the molecular embedding space applying the molecule embedding module a training dataset generated by the aforementioned systems. Then the molecule embedding module is applied to an input molecular dataset to generate a plurality of molecular embeddings. In some instances, each molecule embedding corresponds to at least one molecule included in the input molecular dataset.

Systems and methods are also provided for generating an end-to-end molecular property prediction model. For example, systems are configured to access a molecule embedding module that has been previously trained according to disclosed embodiments herein.

Systems are also configured to access a property prediction module and generate an end-to-end machine learning model configured to predict molecular properties by compiling the molecule embedding module with the property prediction module.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings in which.

DETAILED DESCRIPTION

Embodiments disclosed herein relate to systems, methods, and devices that are configured for generating a training dataset for training a molecule embedding module using contrastive learning, wherein the definition of similarity is based on sharing a molecular scaffold.

In some disclosed embodiments, for example, systems access a molecular dataset and separate the molecular dataset into positive samples and negative samples. Then, the systems generate a training dataset comprising the positive samples and negative samples batches.

Systems and methods are also provided for using the trained molecule embedding module to generate molecule embeddings and for building an end-to-end machine learning model configured to perform molecular embedding analysis and molecular property prediction, the model comprising the trained molecule embedding module and a property prediction module.

The disclosed embodiments provide many technical advantages over existing systems, methods, and devices for generating and using molecular training datasets to train molecule embedding modules configured for determining molecular similarities, as will become apparent from the following disclosure.

For example, a core concept to determine the effectiveness of a molecular embedding approach is called molecular similarity, or the idea that molecules sharing similar structural properties tend to have shorter physical distances in the embedding space while molecules that have dissimilar properties can be separated apart and indicated by low similarity scores. Molecular similarity is fundamental in drug discoveries, with the observation that similar structure fragments of different molecules lead to similar biological activities.

With encoded structural and functional properties, molecular embeddings also help in molecular property prediction tasks related to molecular solubility, toxicity, transport inhibition and so on, as well as interaction tasks across different molecules. In practice, pharmaceutical industries are empowered by molecular virtual screening for compound filtering and selection on millions of compounds, in place of extensive lab experimentation.

Some disclosed embodiments are directed to utilizing molecule-scaffold matching information for molecular embedding space generation in a contrastive learning framework. Thus, by employing shared molecular scaffolding as the definition for molecular similarity during contrastive learning, the molecule embedding module learns how to map molecules to an embedding space by mapping similar molecules close to each other and dissimilar molecules far from one another.

Additionally, since the model is trained in a self-supervised manner, the model is not limited to labeled data, and thus, has the ability to leverage large-scaled unlabeled data sets.

Figure 1:
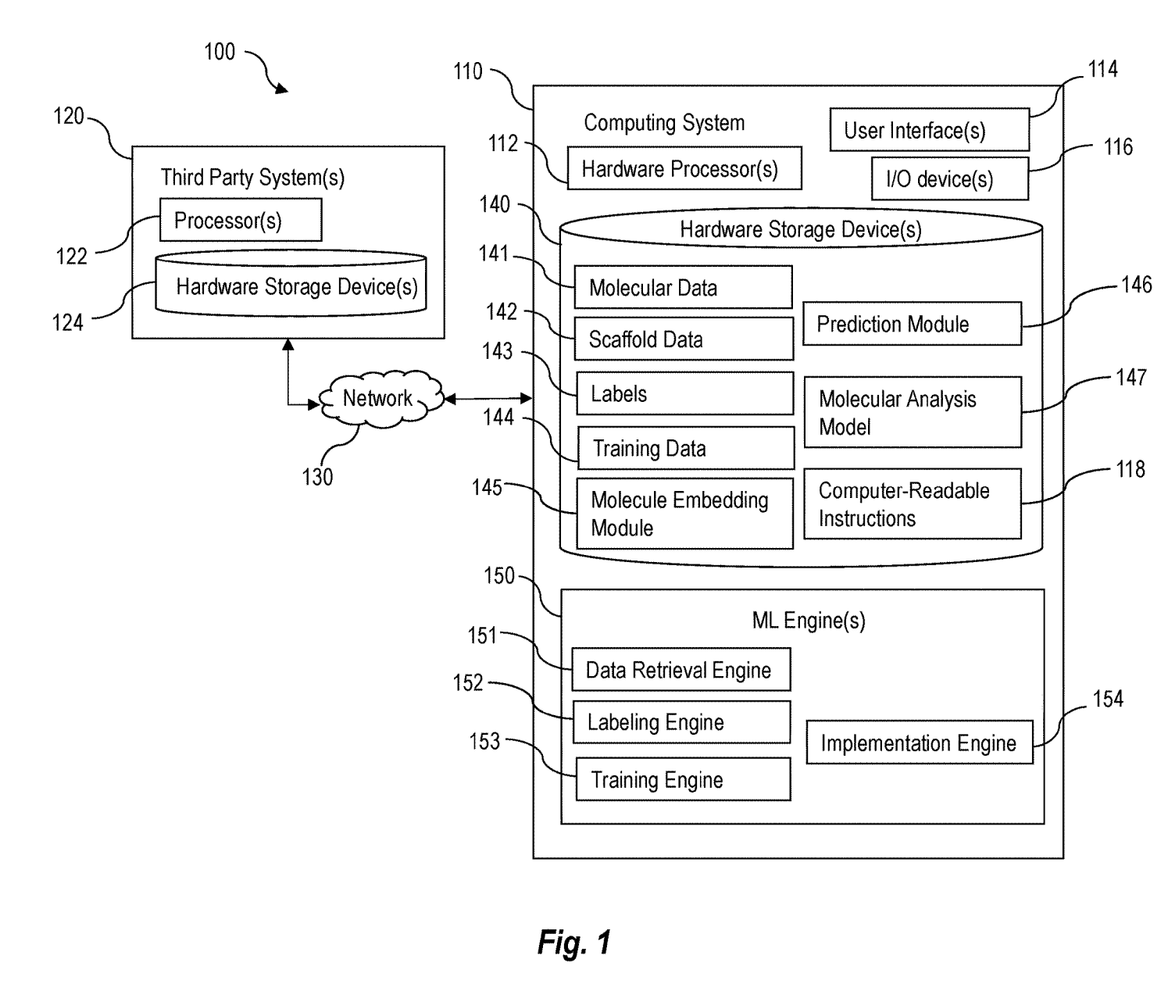
FIG. 1 illustrates an example architecture that includes a computing system that includes and/or that is capable of being utilized to implement the disclosed embodiments.

Attention will now be first directed to FIG. 1, which illustrates a computing system 110 that may include or be used to implement aspects of the claimed invention. In particular, the computing system 110 is configured, as described throughout this disclosure, to generate, train, and operate a multi-modal analysis model configured to generate in-domain multi-modal embeddings and facilitate embedding analysis via contrastive learning.

The computing system 110 is currently illustrated as part of a computing environment 100 that also includes third-party system(s) 120 (which can also be configured as remote systems) in communication (via a network 130) with computing system 110. These remote systems may include distributed portions of the computing system 110.

The computing system 110 is also illustrated as including one or more processor(s) (such as one or more hardware processor(s) 112) and a storage (i.e., hardware storage device(s) 140) storing computer-readable instructions 118 wherein one or more of the hardware storage device(s) 140 is able to house any number of data types and any number of computer-readable instructions 118 by which the computing system 110 is configured to implement one or more aspects of the disclosed embodiments when the computer-readable instructions 118 are executed by the one or more processor(s) 112. The computing system 110 is also shown including user interface(s) 114 and input/output (I/O) device(s) 116.

Hardware storage device(s) 140 is currently shown as a single storage unit. However, it will be appreciated that the hardware storage device(s) 140 is/are also sometimes implemented as a distributed storage which is distributed throughout several separate and sometimes remote systems and/or third-party system(s) 120. In this regard, it will be appreciated that the computing system 110 can comprise a distributed system with one or more of the components of computing system 110 being maintained/run by different discrete systems that are remote from each other and that each perform different tasks. In some instances, for example, the computing system 110 operates as a plurality of distributed systems that perform similar and/or shared tasks for implementing the disclosed functionality, such as in a distributed cloud environment.

The hardware storage device(s) 140 are configured to store the different data types including molecular data 141, scaffold data 142, labels 143, and training data 144, described herein.

In molecular data 141, the data comprises entity data that are molecules or specific molecular sequences. Each molecule can be represented in the molecular dataset comprising a set or sub-set of molecular data 141 in a variety of forms. For example, representation forms include SMILES, IUPAC, and/or a molecular graph. SMILES is an abbreviation for Simplified Molecular Input Line Entry System, a widely known and used database used to represent molecular structures ASCII strings, while IUPAC (the International Union of Pure and Applied Chemistry) provides nomenclature that establishes global standards for names, symbols, and for organizing molecular structures by spoken words.

The molecular data 141 also comprises other molecular property data such as toxicity, heat of combustion, enthalpy of formation, chemical stability in a given environment, flammability, preferred oxidation states, corrosivity, combustibility, acidity, and/or basicity. The molecular data 141 also comprises physical properties such as viscosity, color, opacity, density, etc. The molecular data 141 can also Include drug data, the entities are drugs, including drug names, FDA-approval status, date of FDA-approval, structural information, functional activity information, and drug-drug interaction information, wherein different drugs are based on different molecules.

The scaffold data 142, or molecular scaffold data, comprises one or more molecular scaffolds. Each molecular scaffold corresponds to a particular molecule, or a particular sub-molecule. A molecular scaffold represents the core structure of a molecule. The molecular scaffold also retains underlying characteristics of the molecule.

In some instances, the molecular scaffolds are represented by molecular graphs. Molecular graphs can comprise 2D and/or 3D graphs. 2D graphs can be generated using an open-source toolkit such as RDKit. In the 2D graphs, the molecular structures are represented by line drawings, wherein different molecular configurations take one different 2D shapes. Each node in the graph represents a particular atom in the molecule and each line between two nodes represents the bond between two atoms in the molecule. The scaffold data 142 also includes structural information about each molecule, as well as known biological/chemical activity.

Thus, in some instances, a molecular scaffold is a 2D or 3D representation of the core structure of an entire molecule, wherein a particular molecular scaffold is unique to a particular molecule. Alternatively, a molecular scaffold is a 2D or 3D representation of part of a molecule (e.g., a particular functional group), wherein multiple molecules may comprise a particular molecular scaffold (i.e., may have the same functional group but different variations of atomic configurations/additions of different atoms).

Labels 143 comprise labels for different molecular representation data that comprise the training data. For example, in a particular set or sub-set of molecular data, systems are configured to generate labels which identify positive and negative samples. For example, a label is generated for a particular molecule. When the systems view another molecule that is similar to the first molecule, the same label is generated for the other molecule. If the other molecule is different than the first molecule, a different label is generated for the other molecule. In this manner, molecules with the same label are paired together as positive samples and molecules with different labels are paired together as negative samples. Molecular analysis (i.e., determining whether two molecules are similar or not) is based on molecular scaffold similarity.

The training data 144 comprises molecular data that has been labeled and separated into positive and negative samples/batches of samples (batches) based on having the same scaffold of the molecules included in the training data 144. In some instances, the molecules are represented by molecular graphs and/or molecule embeddings. The training data 144 is configured to train a molecule embedding module to generate molecular embeddings that can be mapped to a molecular embedding space or shared representation space. Similar molecules are mapped closer together based on sharing the same molecular scaffold and dissimilar molecules are mapped further apart based having different molecular scaffolds.

In some instances, "training batch" is used to describe a particular set of training data or a particular training dataset. Similarly, "batch" is used to describe a dataset or a sub-set of a dataset. As used herein, a training batch is referred to as a particular set of positive and negative molecular samples that have been generated by disclosed embodiments. Such training batches are used to pre-train the molecule embedding module to improve training process (i.e., by reducing overall training time of the end-to-end machine learning model).

The storage (e.g., hardware storage device(s) 140) also stores or includes computer-readable instructions 118 that are executable by the systems hardware processors for instantiating or implementing the disclosed models and/or engines shown in computing system 110 (e.g., molecule embedding module 145, property prediction module 146, and/or molecular analysis model 147).

The molecule embedding module 145 is configured to consume molecular graphs, or other molecular representation form, and generate molecule embeddings. The molecule embedding module 145 is first pre-trained (prior to compilation in the molecular analysis model 147) to generate molecule embeddings using a contrastive learning training method. The property prediction module 146 is configured to predict the likelihood that a particular molecular has a target molecular property.

The computing system 110 is configured to build a molecular analysis model 147 that is trainable to perform in-domain embedding analysis. The molecular analysis model 147 is comprised of the molecule embedding module 145 and the property prediction module 146, wherein output from the molecule embedding module 145 is used as input to the property prediction module 146.

The referenced models are configured as machine learning models or machine learned models, such as deep learning models and/or algorithms and/or neural networks. In some instances, the one or more models are configured as engines or processing systems (e.g., computing systems integrated within computing system 110), wherein each engine (i.e., model) comprises its own discrete set of one or more processors (e.g., hardware processor(s) 112) and computer-readable instructions 118.

An additional storage unit for storing machine learning (ML) Engine(s) 150 is presently shown in FIG. 1 as storing a plurality of machine learning models and/or engines. For example, computing system 110 comprises one or more of the following: a data retrieval engine 151, a labeling engine 152, a training engine 153, and an implementation engine 154, which are individually and/or collectively configured to implement the different functionality described herein.

For example, the data retrieval engine 151 is configured to locate and access data sources, databases, and/or storage devices comprising one or more data types from which the data retrieval engine 151 can extract sets or subsets of data to be used as training data or entity data (e.g., new text data/document data/molecular data). The data retrieval engine 151 receives data (e.g., molecular data 141 and/or scaffold data 142) from the databases and/or hardware storage devices, wherein the data retrieval engine 151 is configured to reformat or otherwise augment the received data to be used as training data. Additionally, or alternatively, the data retrieval engine 151 is in communication with one or more remote systems (e.g., third-party system(s) 120) comprising third-party datasets and/or data sources.

The data retrieval engine 151 accesses electronic content comprising various kinds of molecular representations such as textual sequences, ground truth relations among sequences, unlabeled molecular meta information, and/or graphics of molecules. The data retrieval engine 151 is configured to retrieve and generate training datasets comprising data for a target relation. In some instances, if desired format (e.g., textual sequence in a specific format) of the data is not available, the data retrieval engine 151 is able to convert available format to desired format with third party system(s) 120. The data retrieval engine 151 is a smart engine that is able to learn optimal dataset extraction processes to provide a sufficient amount of data in a timely manner as well as retrieve data that is most applicable to the desired applications for which the machine learning models/engines will be trained. For example, the data retrieval engine 151 can learn which databases and/or datasets will generate training data that will train a model (e.g., for a specific query or specific task) to increase accuracy, efficiency, and efficacy of that model in the desired natural language processing techniques.

The data retrieval engine 151 locates, selects, and/or stores raw recorded source data such that the data retrieval engine 151 is in communication with one or more other ML engine(s) and/or models included in computing system 110. In such instances, the other engines in communication with the data retrieval engine 151 are able to receive data that has been retrieved (i.e., extracted, pulled, etc.) from one or more data sources such that the received data is further augmented and/or applied to downstream processes. For example, the data retrieval engine 151 is in communication with the training engine 153 and/or implementation engine 154.

The labeling engine 152 is configured to label the molecular data 141 that is retrieved by the data retrieval engine 151. The labeling engine 152 is configured to identify and label molecules that are determined to be similar or dissimilar based on molecular scaffold analysis. The labeled molecular data is then separated into positive samples and negative samples according to the different labels.

The training engine 153 is in communication with one or more of the data retrieval engine 151 and/or the implementation engine 154. After receiving training data relevant to a particular application or task (e.g., a target relation), the training engine 153 trains one or more models on the training data. The training engine 153 is configured to train a model via unsupervised training, such as self-supervision, or distant supervision, and/or supervised training (i.e., direct supervision). One unsupervised training method is contrastive learning. The training engine 153 is figured to pre-train/train the molecule embedding module 145 on training data to generate molecular embeddings. The training engine 153 is also configured to train the molecular analysis model 147 for a particular molecular analysis task, wherein the molecule embedding module 145 is trained again on a different training dataset than was previously used to pre-train the molecule embedding module 145.

The computing system 110 also includes an implementation engine 154 in communication with any one of the models and/or ML engine(s) 150 (or all of the models/engines) included in the computing system 110 such that the implementation engine 154 is configured to implement, initiate, or run one or more functions of the plurality of ML engine(s) 150. In one example, the implementation engine 154 is configured to operate the data retrieval engines 151 so that the data retrieval engine 151 retrieves data at the appropriate time to be able to generate training data for the training engine 153. The implementation engine 154 facilitates the process communication and timing of communication between one or more of the ML engine(s) 150 and is configured to implement and operate a machine learning model (or one or more of the ML engine(s) 150).

In some embodiments, the implementation engine 154 is configured as a query engine that is configured to receive a query, such as a molecular query, molecular property query, or a drug query and return results that are predicted to be similar to a target entity identified in the query.

The computing system is in communication with third-party system(s) 120 comprising one or more processor(s) 122, one or more of the computer-readable instructions 118, and one or more hardware storage device(s) 124. It is anticipated that, in some instances, the third-party system(s) 120 further comprise databases housing data that could be used as training data, for example, newly discovered molecules not included in local storage. Additionally, or alternatively, the third-party system(s) 120 include machine learning systems external to the computing system 110. The third-party system(s) 120 are software programs or application.

Figure 2:
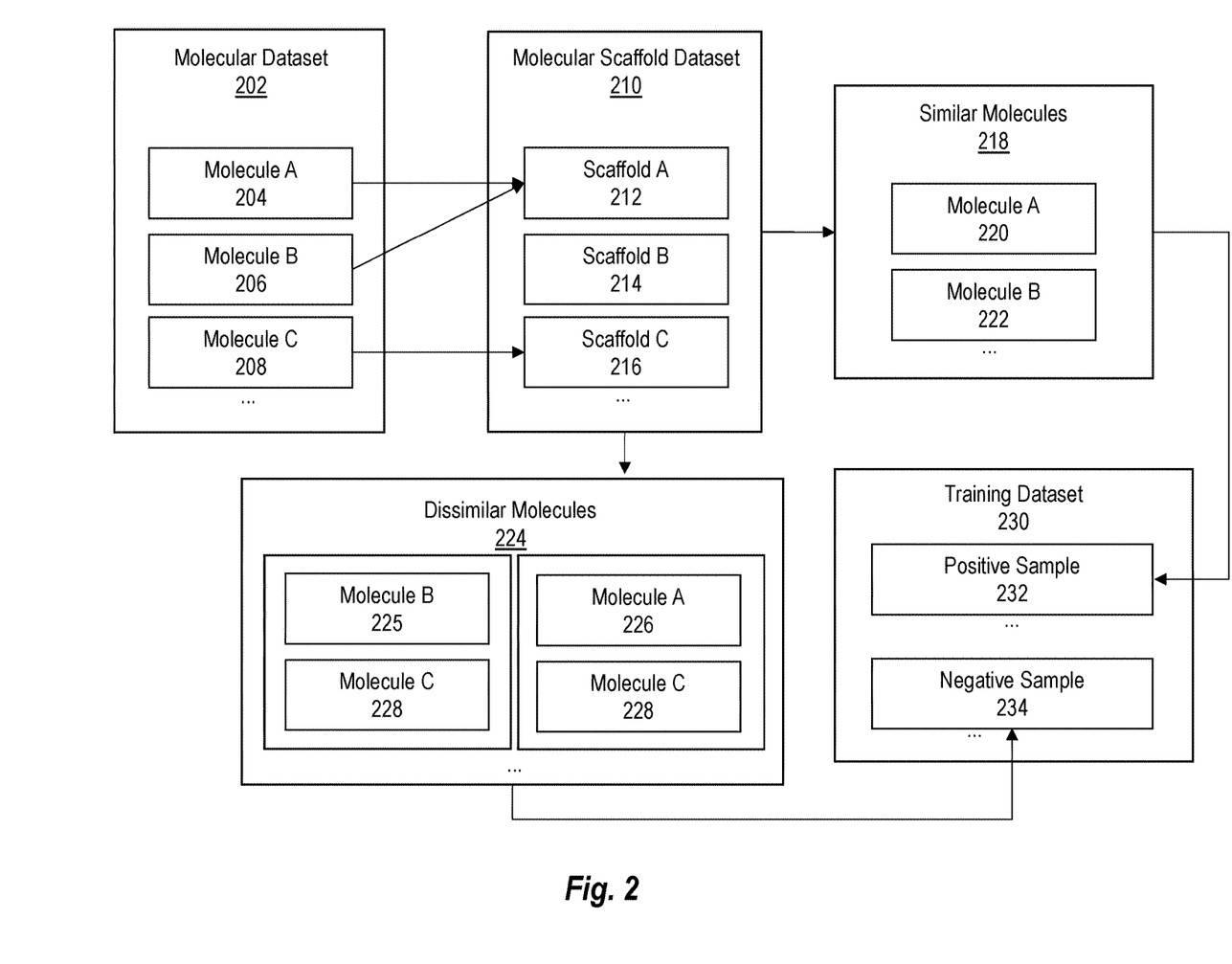
FIG. 2 illustrates an example embodiment of a flow diagram for generating a training dataset configured to train a molecule embedding module.

Attention will now be directed to FIG. 2, which illustrates an example embodiment of a flow diagram for generating a training dataset configured to train a molecule embedding module. FIG. 2 shows a plurality of datasets including a molecular dataset 202, a molecular scaffold dataset 210, similar molecule dataset 218, dissimilar molecule dataset 224, and a training dataset 230. The molecular dataset 202 comprises one or more molecules (e.g., molecule A 204, molecule B 206, molecule C 208, and one or more additional molecules). The molecular scaffold dataset 210 comprises one or more molecular scaffolds (e.g., scaffold A 212 which corresponds to molecule A 204 and molecule B 206 scaffold B 214, and scaffold C 216 which corresponds to molecule C 208, and one or more additional scaffolds which correspond to the one or more additional molecules included in the molecular dataset 202).

The molecular dataset 202 is analyzed and labeled by the system based on whether two molecules share a molecular scaffold. For example, molecule A 204 is determined to be similar to molecule B 206 because molecule A 204 and molecule B 206 correspond to scaffold A 212. Thus, similar molecule dataset 218 comprises at least one similar molecule pair (e.g., molecule A 220 and molecule B 222). Similar molecule dataset 218 comprises one or more additional similar molecule pairs. In contrast, molecule A 204 is determined to be dissimilar to molecule C 208, because molecule A 204 corresponds to scaffold A 212, but molecule C 208 corresponds to scaffold C 216. Additionally, molecule B 206 is determined to be dissimilar to molecule C 208, wherein dissimilar molecule dataset 224 comprises at least one dissimilar scaffold pair (e.g., molecule B 225 and molecule C 228; molecule A 226 and molecule C 228).

Based on the identified similar and dissimilar molecule pairs, the corresponding molecules are separated into one or more positive samples (e.g., positive sample 232 comprising molecule A 204 and molecule B 206 based on both molecules corresponding to the same scaffold, e.g., scaffold A 212) and one or more negative samples (e.g., negative sample 234 comprising molecule B 206 and molecule C 208 based on the each molecule corresponding to a different molecular scaffold).

Training dataset 230 comprises one or more of the positive samples and/or one or more of the negative samples that are used to train the molecule embedding module to map similar molecules close together and also map dissimilar molecules further apart based on their corresponding molecular scaffold structures/analysis.

Figure 3:
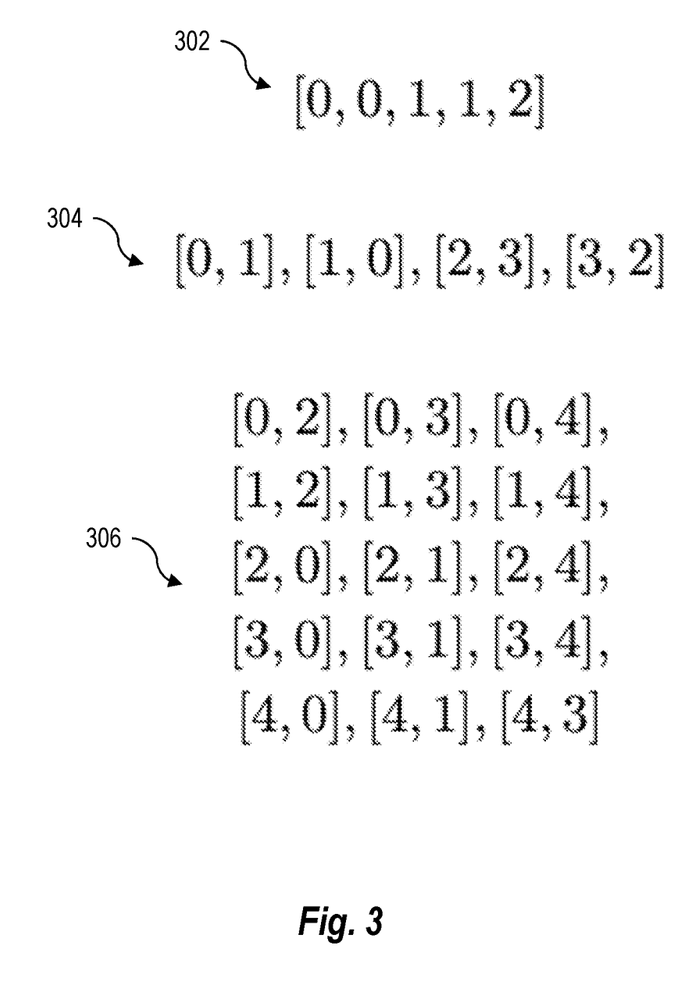
FIG. 3 illustrates an example embodiment a labeled training dataset, for example training dataset of FIG. 2.

Attention will now be directed to FIG. 3, which illustrates an example embodiment a labeled training dataset, for example training dataset of FIG. 2. Another way of describing the generating of the training dataset includes identifying a plurality of molecules, wherein each molecule is labeled with a particular label. For example, in a set of five molecules, each molecule is labeled, wherein similar molecules which have same molecular scaffolds receive similar labels.

The labeled molecular dataset 302 comprises a first molecule labeled 0, a second molecule labeled 0, a third molecule labeled 1, a fourth molecule labeled 1, and a fifth molecule labeled 2. The labeled molecular dataset 302 is then separated into a positive sample dataset 304 and a negative dataset 306. As shown, positive sample dataset 304 includes positive sample pairs of the first molecule and second molecule (e.g., [0,1] and [1,0] and of the third molecule and the fourth molecule (e.g., [2,3] and [3,2]). The negative dataset 306 includes negative sample pairs, wherein the first molecule is dissimilar to the third molecule, fourth molecule, and fifth molecule (e.g., [0,2], [0,3], [0,4], and wherein the second molecular is dissimilar to the third molecule, fourth molecule and fifth molecule (e.g., [1,2], [1,3], [1,4], and wherein the third and fourth molecules are dissimilar to the fifth molecule (e.g., [2,4], [3,4]), among other examples.

Figure 4:
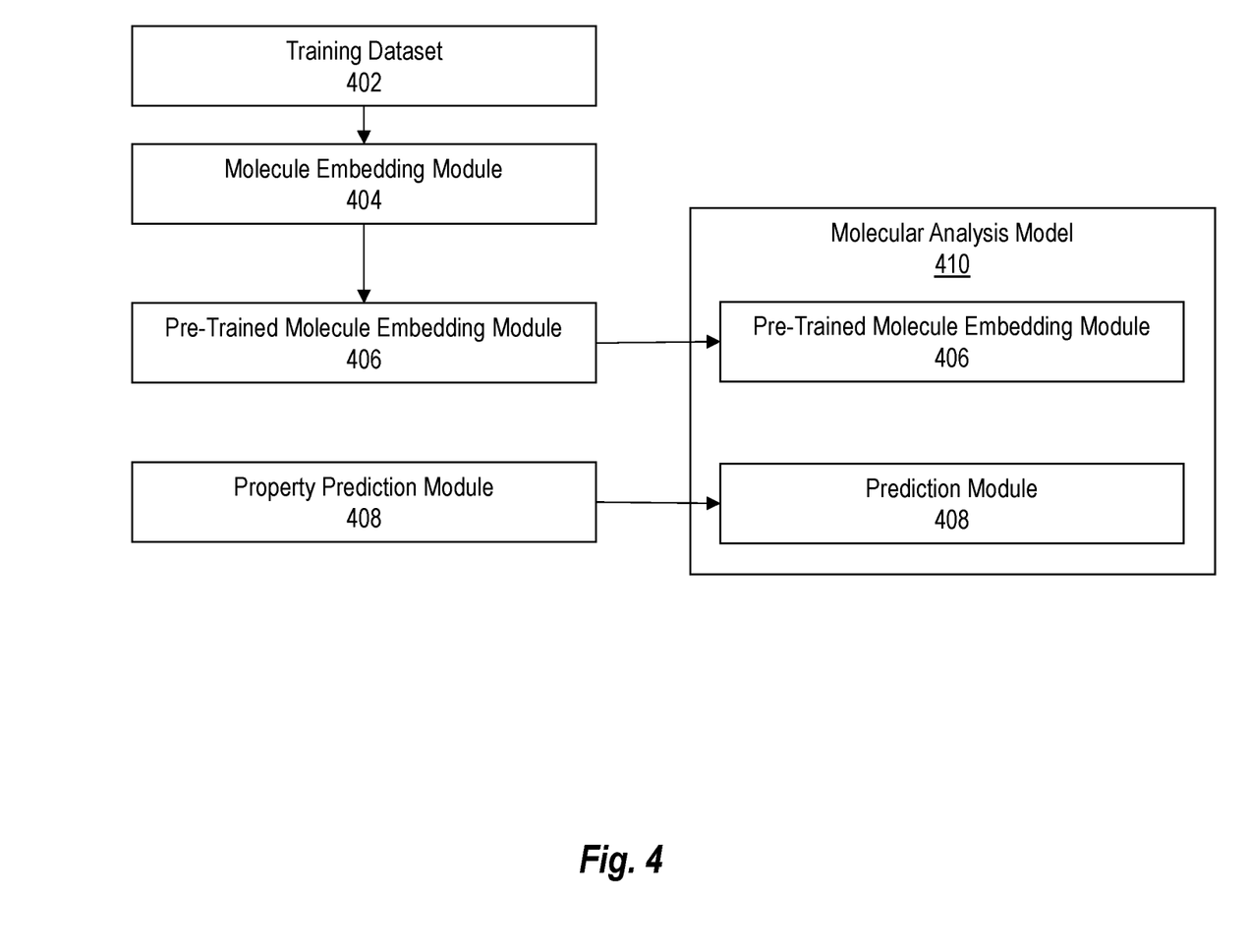
FIG. 4 illustrates an example embodiment for generating an end-to-end molecular prediction machine learning model.

Attention will now be directed to FIG. 4, which illustrates an example embodiment for generating an end-to-end molecular prediction machine learning model. In such embodiments, systems are configured to pre-train the molecule embedding module 404 on the training dataset 402, which is representative of training dataset 230 of FIG. 3 to generate a pre-trained molecule embedding module 406. The systems also access a property prediction module 408. Systems are then configured to generate a molecular analysis model 410 comprising the pre-trained molecule embedding module 406 and the property prediction module 408. Alternatively, systems are configured to access a molecular analysis model 410 and/or generate computer-executable instructions for accessing and/or generating a molecular analysis model 410.

Figure 5:
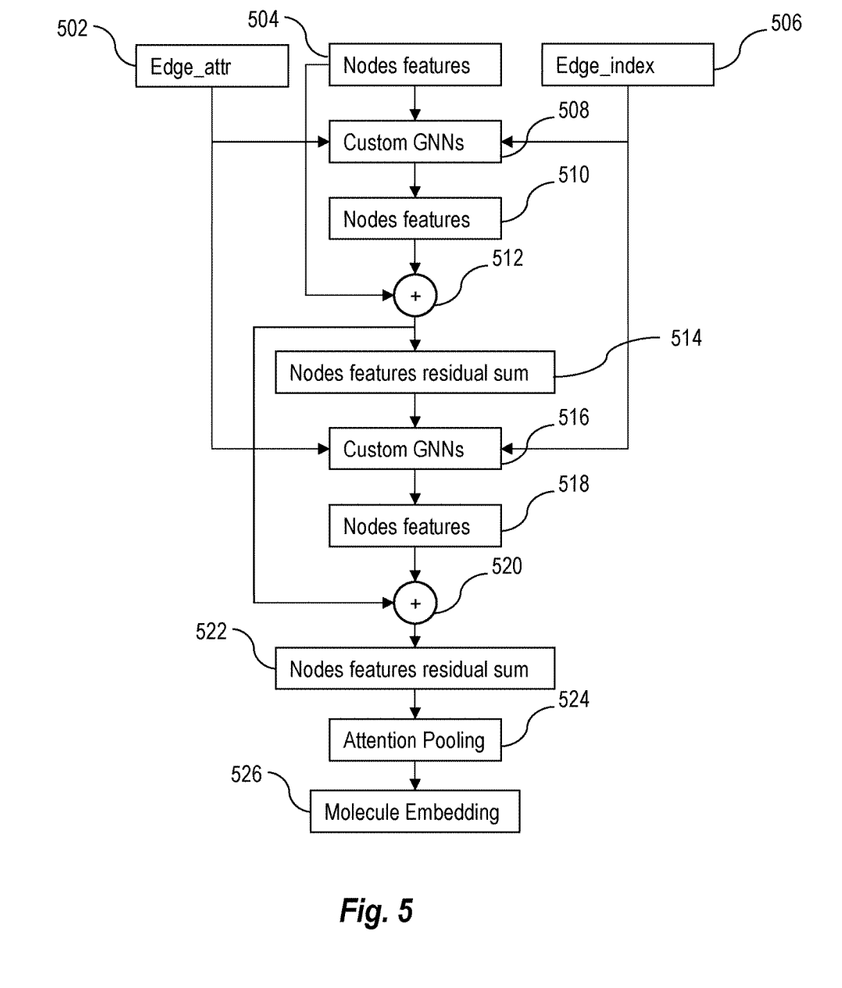
FIG. 5 illustrates an example embodiment of a molecule embedding module, for example molecule embedding module of FIG. 3.

Attention will now be directed to FIG. 5, which illustrates an example embodiment of a molecule embedding module, for example molecule embedding module of FIG. 3. The molecule embedding module consumes a molecule graph as input, in which atoms' properties (e.g., atomic number, atomic charge, etc.) are the basis for node construction features, and in which bonds' properties (e.g., bond direction, bond type, etc.) are the basis for edge construction features The molecule embedding module is based on one or more GNN layers. Graph Neural Networks (GNNs) beneficially provide an effective framework to map the graph representation of a molecule to a feature vector. Using the feature vector, different models that have been trained for various tasks can be applied to the feature vector in order to predict a variety of chemical properties of a molecule. In some instances, the different models employ multi-layer perceptron in order to generate the various predictions.

On each layer, messages are propagated among the connected atoms, where each message is generated based on the features of the neighboring atom and the features of the bond connecting two atoms. A weight is then calculated for each message, wherein the weight specifies the importance of that message in the construction of the receiving node's next hidden state.

While different aggregation methods are applicable, the disclosed embodiments are directed to an aggregation mechanism applied to the message passing process which utilizes the mean, minimum, and maximum aggregations. A residual summation is used to aggregate the features of all the GNN layers and generate the atom's embedding. In the GNN layers, node-features of each layer are based on the input features and the output of the previous GNN layers. Finally, to calculate the molecule's embedding out of all the atoms' embeddings, a global soft attention layer is applied, which works as a soft attention mechanism. The attention layer specifies the importance of each atom's feature vector during aggregation in order to generate the final molecule embedding.

As shown in FIG. 5, the molecule embedding module comprises a plurality of GNN layers (e.g., custom GNNs 508 and custom GNNs 516) which aggregate node and edge features. The first set of GNN layers is configured to receive edge attributes 502, nodes features 504, and access an edge index 506 based on a received molecular input graph. The custom GNNs 508 then compute a set of nodes features 510 for any given node, based on the aggregated features of its neighbors. Finally, the generated features (e.g., nodes features 510) will be aggregated with the input features (e.g., nodes features 504), using a residual summation (e.g., summation 512) to construct a residual feature vector for any given node (e.g., nodes features residual summation 514).

The second set of GNN layers then receive the nodes features residual summation 514 as well as edge attributes 502 and accessing the edge index 506. The second set of GNN layers (e.g., custom GNNs 516) similar to the process described above, generates a new set of features for every node (e.g. nodes features 518), and return the final feature vectors of each node (e.g. nodes feature residual summation 522) using a residual summation (e.g. summation 520), to aggregate the new features (e.g. nodes features 518) with the input features (e.g. nodes features residual summation 514). At the end, a global pooling attention layer 524 is applied to generated nodes features to generate molecule embedding vector 526. The molecule embedding maps molecule 2D structure to point in an N-dimension Euclidian space.

Figure 6:
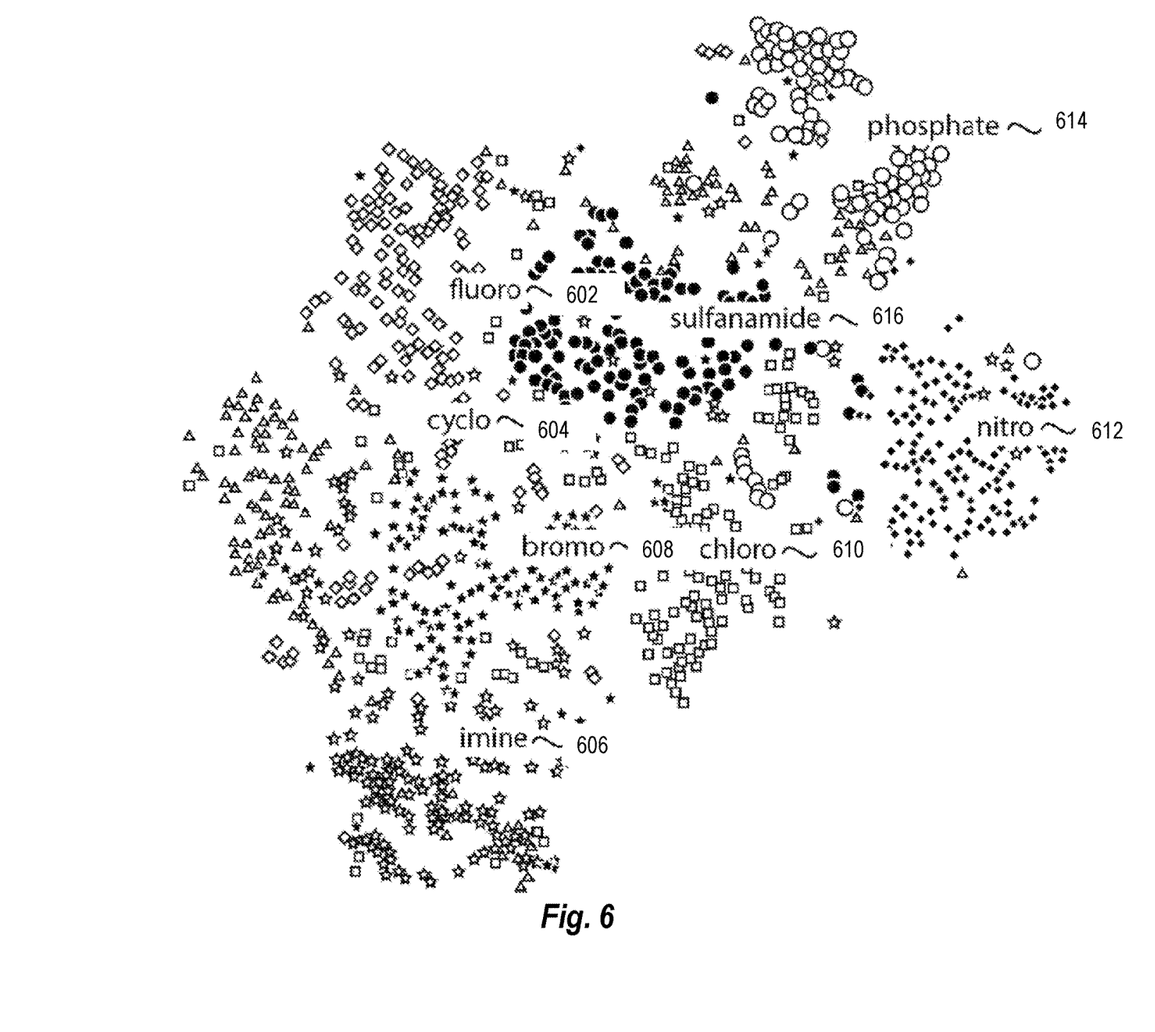
FIG. 6 illustrates an example embodiment of a plurality of molecular embeddings represented in a molecular embedding space.

FIG. 6 illustrates an example embodiment of a plurality of molecules visually represented in a molecular embedding space. As illustrated in FIG. 6, a plurality of molecular embeddings corresponding to the plurality of molecules have been generated by a molecule embedding module as described herein. The plurality of molecules is represented by different shapes. Molecules that have been found to be similar based on corresponding to the same scaffold are mapped close together. For example, molecules represented by stars are mapped close together based on each molecule corresponding to the same scaffold (e.g., a scaffold associated with the imine functional group).

Conversely, molecules that have been found to be dissimilar based on corresponding to different scaffolds are mapped far apart. For example, molecules that are represented by open circles (e.g., that correspond to the same scaffold associated with the phosphate functional group) are mapped far away from the molecules represented by stars (e.g., the imine functional group) because those molecules correspond to different scaffolds. FIG. 6 illustrates a plurality of molecules which correspond to a plurality of different functional groups (e.g., (e.g., fluoro 602, cyclo 604, imine 606, bromo 608, chloro 610, nitro 612, phosphate 614, and suflonamide 616). Each functional group, and therefore the molecules in the functional group, correspond to the same molecular scaffold.

FIG. 6 illustrates an example embodiment of a cluster map for a single modality generated by a machine learning model, for example as depicted in FIG. 5. FIG. 6 displays clustering results based on molecule embeddings generated based on molecular scaffold similarity. Notwithstanding this specific example, it will be appreciated that the clustering is presentable in any modality on which the model is trained. Additionally, clustering is not required. Instead, clustering and cluster mappings are simply one type of graphical illustration that can optionally be prepared, following the other disclosed processes, to visually represent molecules that are determined to be similar based on their scaffold properties.

Figure 7:
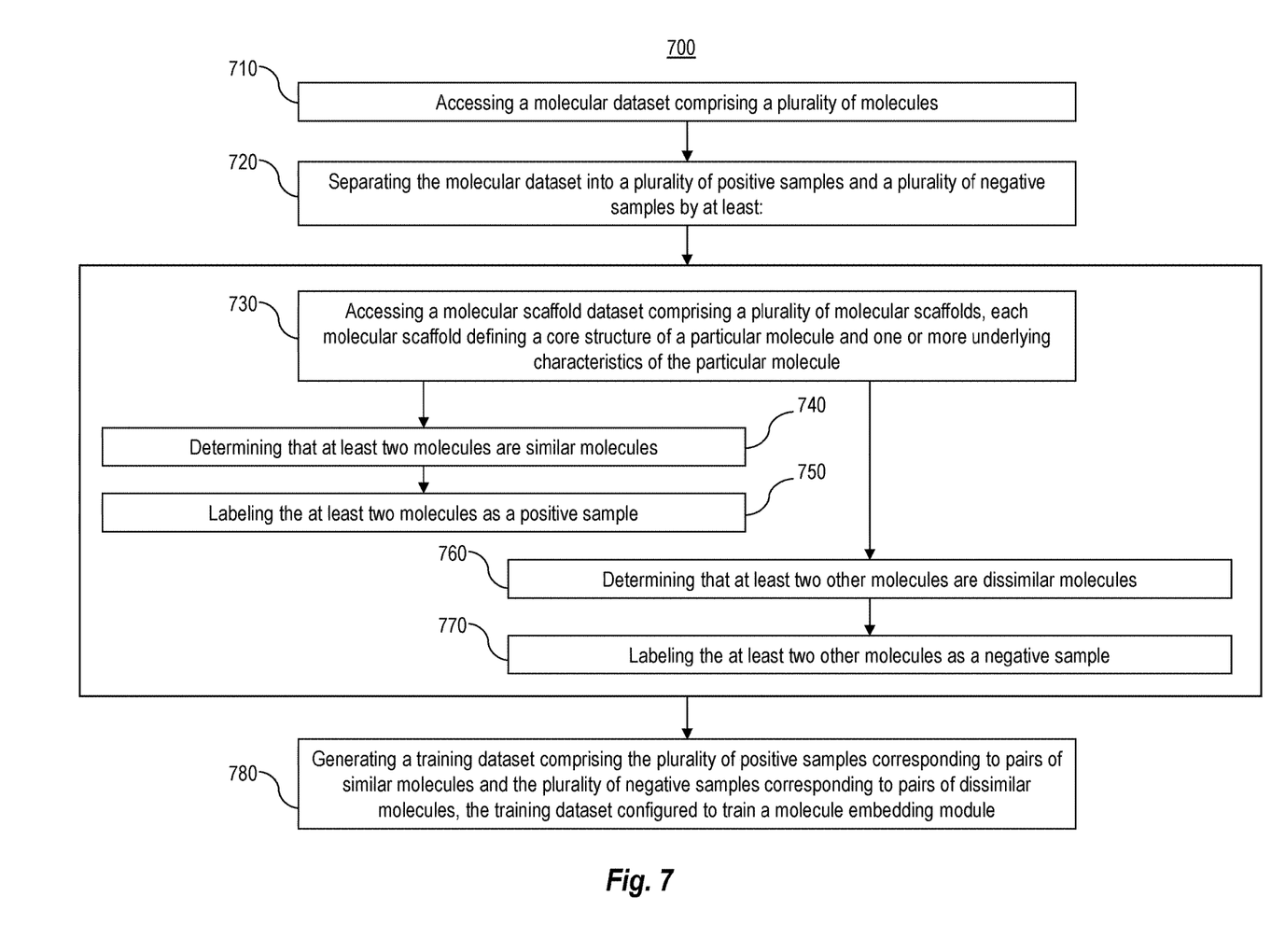
FIG. 7 illustrates a process flow diagram comprising a plurality of acts associated with a method for training a molecule embedding module configured to generate molecular embeddings.
Figure 8:
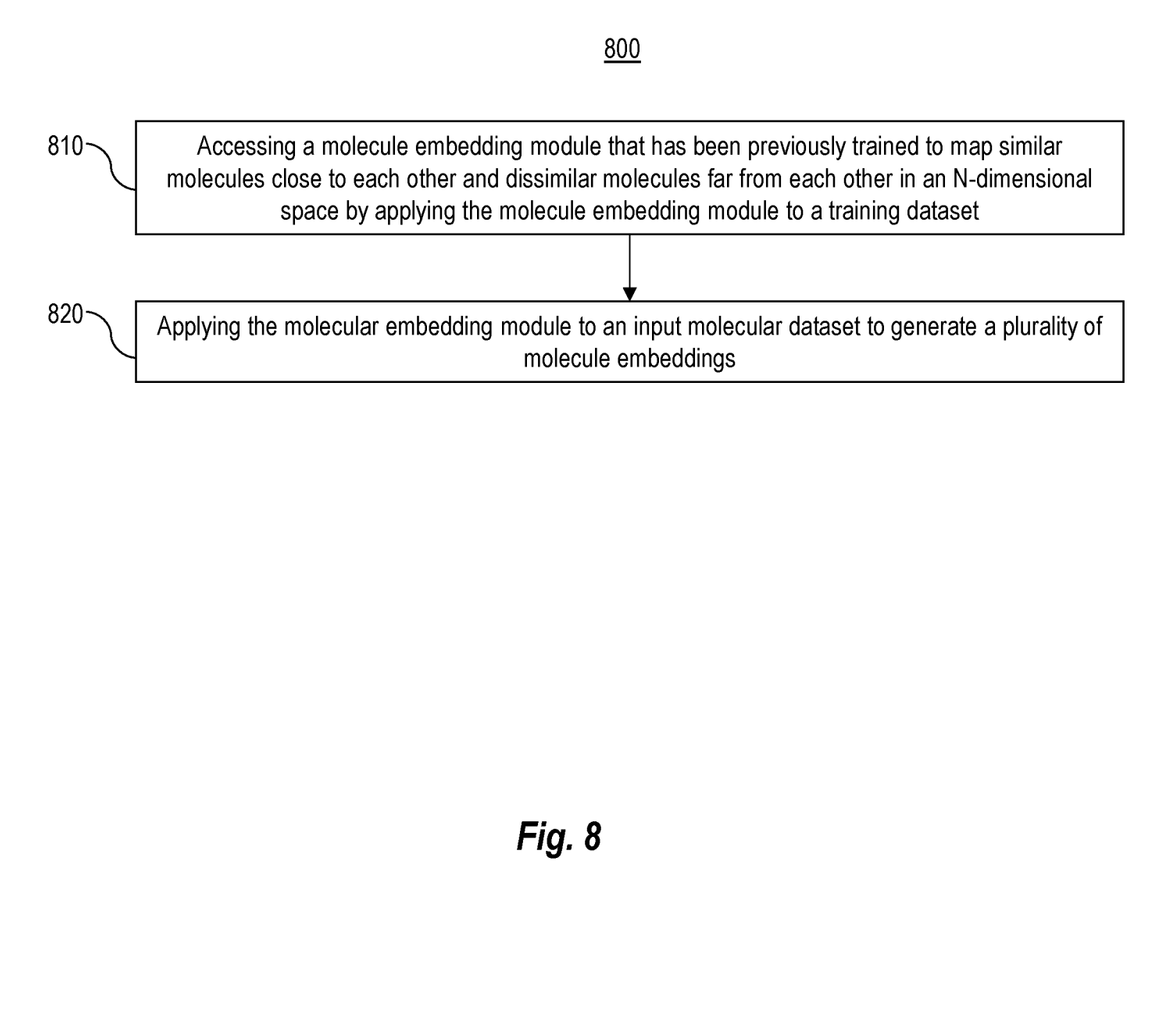
FIG. 8 illustrates a process flow diagram comprising a plurality of acts associated with a method for generating molecular embeddings used a molecule embedding module.
Figure 9:
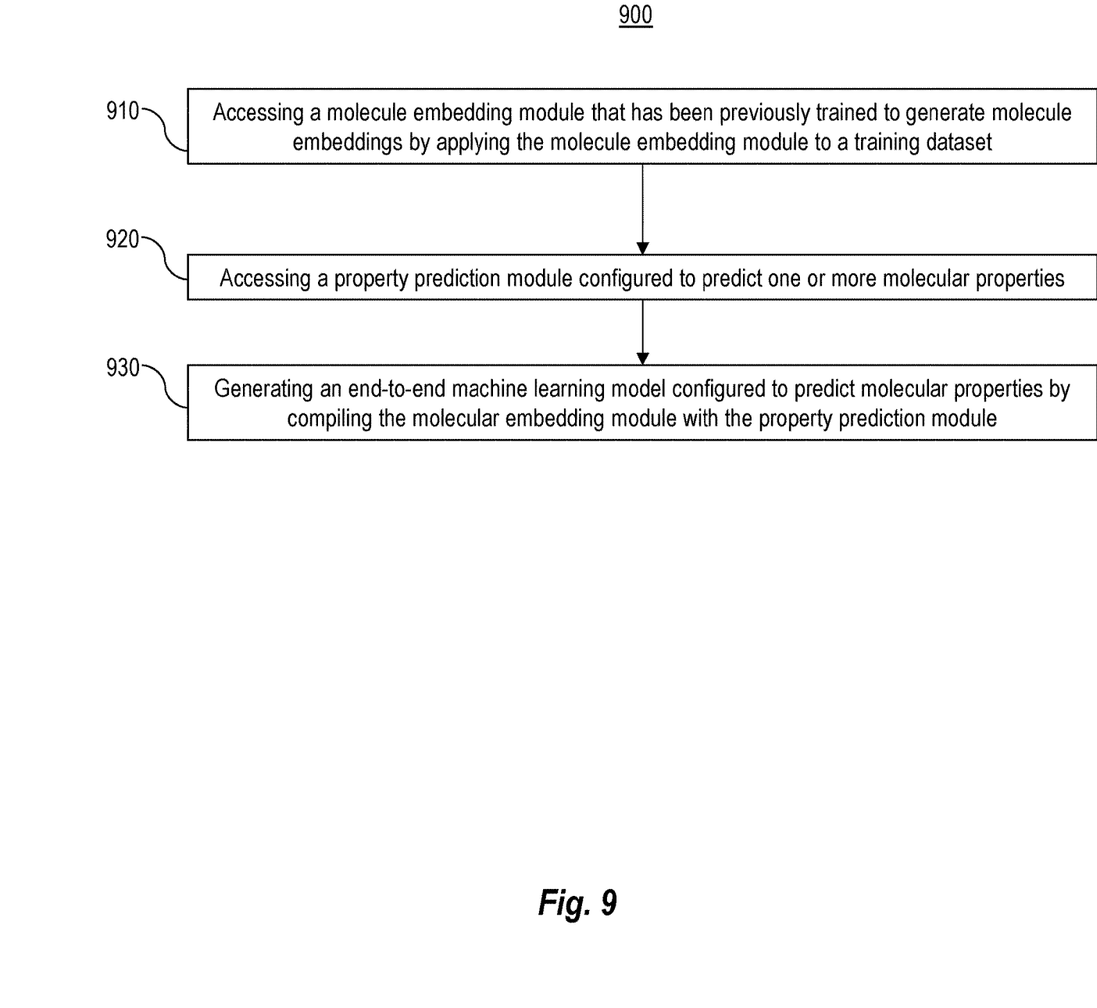
FIG. 9 illustrates a process flow diagram comprising a plurality of acts associated with a method for building an end-to-end molecular prediction machine learning module.

Attention will now be directed to FIGS. 7-9, which illustrates various example embodiments of methods for performing the disclosed embodiments. Although the method acts may be discussed in a certain order or illustrated in a flow chart as occurring in a particular order, no ordering is required unless specifically stated, or required because an act is dependent on another act being completed prior to the act being performed.

FIG. 7 illustrates a flow diagram 700 that includes various acts (act 710, act 720, act 730, act 740, act 750, act 760, and act 770) associated with exemplary methods that can be implemented by computing system 110 for training a molecule embedding module to generate molecular embeddings.

The first illustrated acts are directed to accessing a molecular dataset comprising a plurality of molecules (act 710) and separating the molecular dataset into a plurality of positive samples and a plurality of negative samples (act 720).

The molecular dataset is separated by a plurality of corresponding acts including, accessing a molecular scaffold dataset comprising a plurality of molecular scaffolds (act 730). As previously mentioned, each molecular scaffold defines a core structure of a particular molecule and one or more underlying characteristics of the particular molecule. The systems are also configured to determine when at least two of the other molecules are dissimilar based on whether they correspond to different scaffolds(act 760, and to responsively label the at least two other molecules as a negative sample (act 770).

After the molecular dataset has been labeled and separated, the systems are configured to generate a training dataset comprising the plurality of positive samples corresponding to pairs of similar molecular scaffolds and the plurality of negative samples corresponding to pairs of dissimilar molecular scaffolds, the training dataset configured to train a molecule embedding module (act 780).

By generating a training dataset based on molecular scaffold similarity, the molecule embeddings retain information about the structure of the molecule, as well as underlying characteristics of the molecule. This improves the quality of downstream tasks, including molecular property prediction.

After the training dataset is generated, the systems are configured to apply the molecule embedding module to the training dataset to train the molecule embedding module to generate molecule embeddings. After training, the molecule embedding module is ready to be applied to an input molecular dataset comprising a plurality of molecules, wherein the molecule embedding module is configured to generate a plurality of molecule embeddings and wherein each molecule embedding corresponds to a molecule included in the input molecular dataset.

To fully benefit from this implementation, a data-loader (e.g., data retrieval engine 151) is utilized that generates batches of molecular data with unique scaffold pairs to be used in the training dataset. In such instances, a molecule is only added to the batch if and only if no other molecule with the same scaffold is already in that batch. If no other molecule with the same scaffold is identified, then the scaffold of that molecule will be added as a positive sample for that molecule and the instances are labeled accordingly. As a result, for each molecule in the batch, its scaffold will have the same label, and every other molecule in that batch will have a different label (which forms the basis of negative samples).

Thus, in some instances, flow diagram 700 optionally includes acts directed to adding a new molecule to a training batch by identifying a target molecule to be added to the training batch, identifying a particular molecular scaffold associated with the target molecule, determining that no other molecule included in a training batch is associated with the particular molecular scaffold, and in response to determining that no other molecule included in a training batch is associated with the particular molecular scaffold, adding the target molecule to a training batch.

Conversely, flow diagram 700 optionally includes acts directed to refraining from adding a new molecule to the a training batch by identifying a target molecule to be added to a training batch, identifying a particular molecular scaffold associated with the target molecule, determining that at least one other molecule included in a training batch is associated with the particular molecular scaffold, and in response to determining that at least one other molecule included in a training batch is associated with the particular molecular scaffold, refraining from adding the target molecule to the molecular dataset.

By generating the training dataset in this manner, the systems beneficially provide a unique set of molecules for the molecule embedding module to be trained on, without the redundancy of duplicate molecules which would provide no new information for the molecule embedding module to learn. Additionally, using contrastive learning provides an unsupervised training method that is able to utilize large sets of unlabeled data.

Attention will now be directed to FIG. 8, which illustrates a process flow diagram comprising a plurality of acts associated with a method for generating molecular embeddings used a molecule embedding module. FIG. 8 illustrates a flow diagram 800 that includes various acts (act 810 and act 820) associated with exemplary methods that can be implemented by computing system 110 for generating molecular embeddings.

The first illustrated act is directed to accessing a molecule embedding module that has been previously pre-trained, by learning how to map molecules with the same scaffold close to each other and molecules with different scaffolds far apart in an N-dimensional space (act 810). The training dataset is generated, for example, by the method depicted by flow diagram 800 in FIG. 8. By generating a training dataset based on molecular scaffold similarity, the molecule embeddings retain information about the structure of the molecule, as well as underlying characteristics of the molecule. This improves the quality of downstream tasks, including molecular property prediction.

Systems then apply the molecule embedding module to an input molecular dataset to generate a plurality of molecule embeddings, each molecule embedding corresponding to at least one molecule included in the input molecular dataset (act 820). In some instances, the input molecular dataset comprises a plurality of molecular graphs. The molecule embeddings that are generated retain information about the structure of the molecule, as well as underlying characteristics of the molecule.

Attention will now be directed to FIG. 9, which illustrates a process flow diagram comprising a plurality of acts associated with a method for building an end-to-end molecular prediction machine learning module. FIG. 9 illustrates a flow diagram 900 that includes various acts (act 910, act 920, and act 930) associated with exemplary methods that can be implemented by computing system 110 for building an end-to-end machine learning model configured to perform molecular analysis and prediction tasks.

As shown in FIG. 9, the first illustrated act is directed to accessing a molecule embedding module that has been previously trained to map molecules with the same scaffolds close to each other and molecules with different scaffolds far apart by applying the molecule embedding module to a training dataset (act 910). The training dataset is generated, for example, according to the methods described above.

The systems are also configured to access a property prediction module configured to predict one or more molecular properties (act 920). After accessing the molecule embedding module and the property prediction module, the systems are configured to generate an end-to-end machine learning model configured to predict molecular properties by compiling the molecular embedding module with the property prediction module (act 930).

In some embodiments, systems are provided for applying the molecule embedding module to an input molecular dataset comprising a plurality of molecules, and generating a plurality of molecule embeddings, each molecule embedding corresponding to a molecule included in the input molecular dataset.

In summary, contrastive learning is used to pre-train the molecule embedding module. The pre-trained molecule embedding module is used in an end-to-end machine learning model, and then re-trained to predict specific chemical properties of different sets of molecules.

Thus, once an end-to-end model is generated and trained, systems are configured to receiving a user input comprising a query to find one or more candidate molecules that are predicted to be similar to a target molecule, identify one or more candidate molecules that are predicted to be similar to the target molecule based on the molecular cluster map, and return to a user a list of one or more candidate molecules.

Based on the list of one or more candidate molecules, systems are provided for identifying a particular molecular property associated with the one or more candidate molecules and using the property prediction module to predict that the target molecule is associated with the particular molecular property based on a similarity score to the one or more candidate molecules.

Because the molecule embedding module was pre-trained using contrastive learning based on molecular scaffold similarity, the downstream prediction will have a higher accuracy, as the embedding module has learned to embed some information of a molecule during the pre-training process.

In view of the foregoing, it will be appreciated that the disclosed embodiments provide many technical benefits over conventional systems and methods for building, training, and utilizing machine learning models for in-domain multi-modal embedding analysis, including training a molecule embedding module using contrastive learning, wherein molecular similarity is defined by the molecular scaffold of the different molecules.

Example Computer Systems

Embodiments of the present invention may comprise or utilize a special purpose or general-purpose computer (e.g., computing system 110) including computer hardware, as discussed in greater detail below. Embodiments within the scope of the present invention also include physical and other computer-readable media for carrying or storing computer-executable instructions and/or data structures, which are executable for configuring the disclosed systems to implement the disclosed functionality. Such computer-readable media can be any available media that can be accessed by a general purpose or special purpose computer system.

Computer-readable media (e.g., hardware storage device(s) 140 of FIG. 1) that store computer-executable instructions (e.g., computer-readable instructions 118 of FIG. 1) are physical hardware storage media/devices that exclude transmission media. Computer-readable media that carry computer-executable instructions or computer-readable instructions (e.g., computer-readable instructions 118) in one or more carrier waves or signals are transmission media. Thus, by way of example, and not limitation, embodiments of the invention can comprise at least two distinctly different kinds of computer-readable media: physical computer-readable storage media/devices and transmission computer-readable media.

Physical computer-readable storage media/devices are hardware and include RAM, ROM, EEPROM, CD-ROM or other optical disk storage (such as CDs, DVDs, etc.), magnetic disk storage or other magnetic storage devices, or any other hardware which can be used to store desired program code means in the form of computer-executable instructions or data structures and which can be accessed by a general purpose or special purpose computer.

A "network" (e.g., network 130 of FIG. 1) is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmission media can include a network and/or data links which can be used to carry, or desired program code means in the form of computer-executable instructions or data structures, and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general-purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

The present invention may be embodied in other specific forms without departing from its essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for generating training batches for training a molecule embedding module configured to be used in an end-to-end model configured to predict molecular properties, the method executed by one or more computer processors comprising:

accessing a molecular dataset comprising a plurality of molecules; and separating the molecular dataset into a plurality of positive samples and a plurality of negative samples by at least:

accessing a molecular scaffold dataset comprising a plurality of molecular scaffolds, each molecular scaffold defining a core structure of a particular molecule and one or more underlying characteristics of the particular molecule;

determining that at least two molecules included in the plurality of molecules are similar based on the at least two molecules corresponding to a same molecular scaffold;

labeling the at least two molecules as a positive sample;

determining that at least two other molecules included in the plurality of molecules are dissimilar based on the at least two other molecules corresponding to different molecular scaffolds;

labeling the at least two other molecules as a negative sample; and generating a training batch comprising the plurality of positive samples corresponding to pairs of similar molecules and the plurality of negative samples corresponding to pairs of dissimilar molecules, the training batch configured to train the molecule embedding module using contrastive learning;

applying the molecule embedding module to a training dataset to train the molecule embedding module to generate molecule embeddings using the contrastive learning;

applying the molecule embedding module to an input molecular dataset comprising a plurality of molecules; and generating a plurality of molecule embeddings, each molecule embedding corresponding to a molecule included in the input molecular dataset.

2. The method of claim 1, further comprising:
identifying a target molecule to be added to the training batch;
identifying a particular molecular scaffold associated with the target molecule;
determining that no other molecule included in the training batch is associated with the particular molecular scaffold; and
in response to determining that no other molecule included in the training batch is associated with the particular molecular scaffold, adding the target molecule to the training batch.

3. The method of claim 1, further comprising:
identifying a target molecule to be added to the training batch;
identifying a particular molecular scaffold associated with the target molecule;
determining that at least one other molecule included in the training batch is associated with the particular molecular scaffold; and
in response to determining that at least one other molecule included in the training batch is associated with the particular molecular scaffold, refraining from adding the target molecule to the training batch.

4. The method of claim 1, wherein the molecule embedding module comprises one or more graph neural network layers.

5. A method for identifying positive samples from a set of molecular in order to map similar molecules close to each other in a molecular embedding space, the method executed by one or more computer processors comprising:

(i) accessing a molecule embedding module that has been previously trained to map similar molecules close to each other, and dissimilar molecules far apart, the molecule embedding module having been previously trained by a process that includes at least:

accessing a molecular dataset comprising a plurality of molecules; and separating the molecular dataset into a plurality of positive samples and a plurality of negative samples by at least:

accessing a molecular scaffold dataset comprising a plurality of molecular scaffolds, each molecular scaffold defining a core structure of a particular molecule and one or more underlying characteristics of the particular molecule;

determining that at least two molecules are similar molecules;

labeling the at least two molecules as a positive sample;

determining that at least two other molecules are dissimilar molecules and labeling the at least two other molecules as a negative sample; and generating a training batch comprising the plurality of positive samples corresponding to pairs molecules corresponding to a same molecular scaffold and the plurality of negative samples corresponding to pairs of dissimilar molecules which correspond to different molecular scaffolds; and (ii) applying the molecule embedding module to an input molecular dataset to generate a plurality of molecule embeddings, each molecule embedding corresponding to at least one molecule included in the input molecular dataset, wherein the input molecular dataset comprises a plurality of molecular graphs; and identifying positive molecular samples and negative molecular samples from the plurality of molecule embeddings, wherein each positive molecular sample is identified based on a similar molecular scaffold and each negative molecular sample is identified based on dissimilar molecular scaffold.

6. A method for building an end-to-end machine learning model configured to predict molecular properties, the method executed by one or more computer processors comprising:

(i) accessing a molecule embedding module that has been previously trained to map similar molecules close to each other and dissimilar molecules far apart in an embedding space, by applying the molecule embedding module to a training dataset, the training dataset being generated by a process that includes at least:

accessing a molecular dataset comprising a plurality of molecules;

separating the molecular dataset into a plurality of positive samples and a plurality of negative samples by at least:

accessing a molecular scaffold dataset comprising a plurality of molecular scaffolds, each molecular scaffold defining a core structure of a particular molecule and one or more underlying characteristics of the particular molecule, determining that at least two molecules are similar molecules, labeling the at least two molecules as a positive sample, determining that at least two other molecules are dissimilar molecules and labeling the at least two other molecules as a negative sample; and generating a training batch comprising the plurality of positive samples corresponding to pairs of molecules corresponding to a same molecular scaffold and the plurality of negative samples corresponding to pairs of dissimilar molecules which correspond to different molecular scaffolds; and (ii) accessing a property prediction module configured to predict one or more molecular properties; and (iii) generating an end-to-end machine learning model configured to predict molecular properties by compiling the molecular embedding module with the property prediction module;

applying the molecule embedding module to an input molecular dataset comprising a plurality of molecules;

generating a plurality of molecule embeddings, each molecule embedding corresponding to a molecule included in the input molecular dataset;

identifying a particular molecular property associated with one or more candidate molecules; and using the property prediction module to predict that a target molecule is associated with the particular molecular property based on a similarity score to the one or more candidate molecules.

7. The method of claim 6, wherein the molecule embedding dataset comprises a plurality of molecular graphs.

8. The method of claim 6, wherein the molecule embedding graph comprises one or more graph neural networks.

* * * * *